United States Patent [19]

Phillips et al.

[11] Patent Number: 4,834,097
[45] Date of Patent: May 30, 1989

[54] CARDIO-VALVE ASSIST UNIT AND METHOD FOR PERFORMING CARDIO-VALVE REPLACEMENT SURGERY

[75] Inventors: James L. Phillips; Dale W. Richardson, both of Mattawan, Mich.; J. Donald Hill, San Francisco, Calif.

[73] Assignee: Richardson & Associates, Ltd., Kalamazoo, Mich.

[21] Appl. No.: 176,030

[22] Filed: Mar. 31, 1988

[51] Int. Cl.$^4$ .............................................. A63B 17/04
[52] U.S. Cl. ............................ 128/334 R; 128/303 R
[58] Field of Search ................... 269/45, 238, 328, 97; 248/125, 225.31, 229, 285, 540; 128/303 R, 334 R, 346, 303 B; 623/2, 900, 66

[56] References Cited

U.S. PATENT DOCUMENTS

| | | | |
|---|---|---|---|
| 602,055 | 12/1898 | Campbell | 248/225.31 |
| 2,711,872 | 6/1955 | Lampke | 248/229 |
| 3,409,013 | 11/1968 | Berry | 623/66 |
| 3,587,115 | 6/1971 | Shiley | 128/334 R |
| 3,628,535 | 12/1971 | Ostrowsky et al. | 128/303 R |
| 4,585,453 | 4/1986 | Martin et al. | 623/2 |

FOREIGN PATENT DOCUMENTS

| | | | |
|---|---|---|---|
| 207339 | 2/1968 | U.S.S.R. | 128/334 R |
| 252000 | 2/1970 | U.S.S.R. | 128/303 R |
| 782808 | 11/1980 | U.S.S.R. | 128/303 R |
| 969264 | 10/1982 | U.S.S.R. | 623/2 |

Primary Examiner—Richard C. Pinkham
Assistant Examiner—Gary Jackson
Attorney, Agent, or Firm—Gordon W. Hueschen

[57] ABSTRACT

There is disclosed a method for effecting cardio-valve replacement surgery. A clamp adapted to be fastened to an ether screen has multiple arms. These arms are linked together by a double clamp having two parts which are pivotable with respect to each other and within which the arms are both rotatable and slidable and which arms are simultaneously clamped in whatever position they may have been set. The clamping is effected by a draw bolt passing through both parts of the double clamp. At the free end of the arms is a clamp adapted to hold a replacement cardio-valve holder. The clamps and the arms are adjusted to present a replacement valve in a position such that it can be sutured into the heart of the patient without the surgeon having concern about the possibility of malalignment of the valve or suturing.

5 Claims, 2 Drawing Sheets

CARDIO-VALVE ASSIST UNIT AND METHOD FOR PERFORMING CARDIO-VALVE REPLACEMENT SURGERY

BACKGROUND OF THE INVENTION

Field of the Invention and Prior Art

The present invention relates to a method for performing cardio-valve replacement surgery.

Effective cardio-valve replacement surgery requires that the replacement valve be handled very carefully. To this end special valve holders have been developed so that the replacement valve can be properly held in the proper place during suturing of the replacement valve into the heart. Heretofore, however, there has been no effective means for holding the replacement valve holder during the suturing and as a result there sometimes occurs an inadvertent malalignment which results in a less-than desired positioning or suturing.

OBJECTS OF THE INVENTION

It is an object of this invention to provide such method and to avoid the disadvantage of the prior art. It is a further object of the invention to obtain such advantages. Other objects will be apparent to one skilled in the art and still others will become apparent as the description proceeds.

SUMMARY OF THE INVENTION

The invention inter alia relates to a method of performing cardio-valve replacement surgery using a cardio-valve assist unit which comprises:

first clamp means adapted to be clamped in a fixed position relative to an operating table;

first arm means affixed to said first clamp means and rigidly projecting therefrom;

second arm means;

double-clamp means for connecting said second arm means to said first arm means;

said double-clamp means comprising two parts mounted for rotation one relative to the other, one of which is adapted to receive said first arm means for slidable and preferably also rotatable movement therein and the other of which is adapted to receive said second arm means for slidable and preferably also rotatable movement therein, and a single clamping screw means adapted simultaneously to clamp said two parts on said arm means in any position to which they may have been adjusted; and third clamp means mounted on said second arm means for clamping a cardio-valve holding means to said second arm, preferably rigidly affixed thereto and preferably in a position substantially normal thereto and adjacent one end thereof;

whereby, when a cardio-valve holding means having a cardio-valve therein is set in said third clamp means, the cardio-valve can be placed in position for suturing into the heart and held firmly in that position until the suturing is completed.

The invention also relates to one or more further features in which each of the parts of said double clamp means comprises split-ring clamps; in which said double clamp means comprises a draw bolt which projects through the split ring clamps and is adapted to tighten them simultaneously into a fixed position relative to each other and also onto both arms; and/or in which said third clamp means comprises a bore having a larger end tapering to a smaller end and screw means threaded thereinto for movement toward said small end, whereby different-sized arms of different cardio-valve holders can be inserted therein and clamped tightly against said tapering walls.

The invention also relates to a method for performing cardio-valve replacement surgery which comprises, in any order:

affixing a replacement cardio-valve in a cardio-valve holding means;

adjusting said cardio-valve holding means into a position where the replacement cardio-valve can be sutured into the heart;

clamping it rigidly in that position relative to the operating table; and thereafter suturing the replacement cardio-valve into the heart.

The invention preferably comprises such a method in which the adjusting and clamping steps are effected with the employment of a cardio-valve assist unit as described above.

DETAILED DESCRIPTION OF A PREFERRED EMBODIMENT

Figure 1:
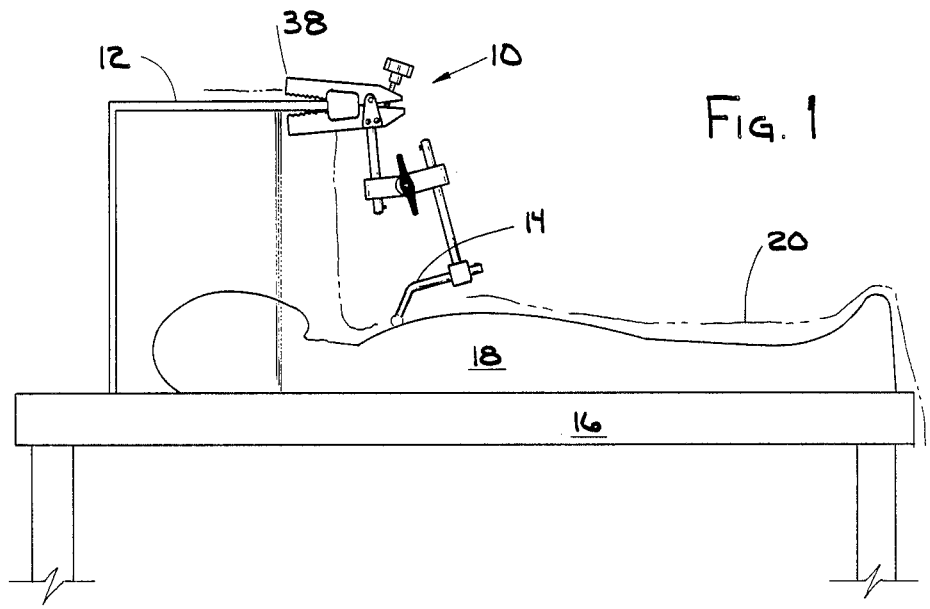
FIG. 1 is a face view showing generally the apparatus and method of the invention.
Figure 2:
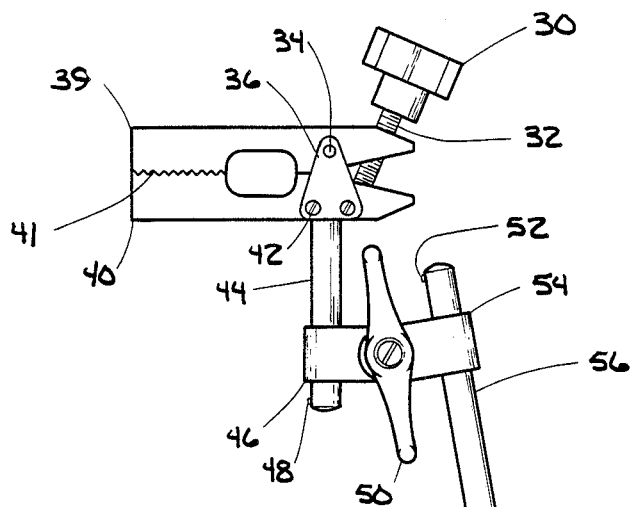
FIG. 2 is a face view of the cardio-valve assist unit of the invention.
Figure 2:
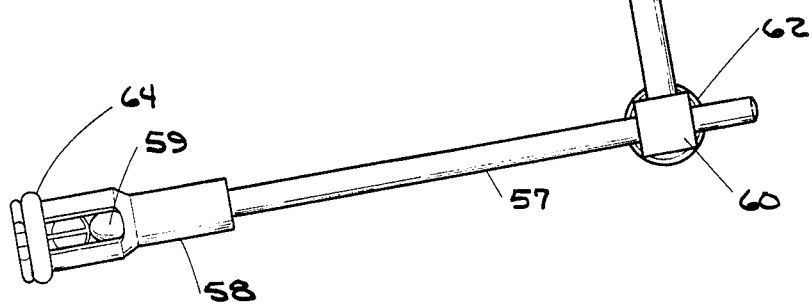

FIG. 1 shows the general layout of the invention and illustrates how the cardio-valve assist unit 10 of the invention is used. A clamp 38 is fastened to an ether screen 12 at the head of operating table 16. An outline of the patient to be operated upon is shown at 18. On the unit 10 there is mounted a cardio-valve holding device 14 of any suitable design adapted to hold a cardio-valve replacement in position for the surgeon to suture it into the heart of the patient.

The clamp 38 has opposed jaws 39 and 40 which are pivoted at one end. The pivot comprises plates 36, one on each side, which are fastened to one jaw 40 by screws 42 and to the other by an aperture and pivot 34. The jaws ar adapted to open to the position shown in FIG. 1 where they are clamped on the ether screen 12 by turning the knob 30 which actuates screw 32. The jaws may have saw-teeth or some form of knurling 41 to provide a good grip on the ether screen. If an ether screen is not used, a transverse bar mounted on suitable supports, not shown, can be placed over the patient in the vicinity of the neck. In such a case, it may be desirable to invert the clamp inasmuch as the construction thereof, which will be described in more detail, is such as to admit of use in either position depending on the exact location and height of the support for the clamp above the patient.

The fixed jaw 40 of the clamp 38 has an arm 44 projecting essentially normally thereto. Advantageously, it is a rod. In other embodiments, the arm or rod 44 may be on the upper jaw member 39, which may or may not be the fixed jaw member, and/or the arm or rod 44 may project through the one clamp jaw into the other jaw or into a recess therein, a structure particularly useful when securement of the clamp to or around a bar or other relatively narrow structural element is required.

To said arm or rod 44 is fastened a further clamp member 46, which can be referred to as a split-ring clamp, and which has a bore adapted to rotatably and slidably receive the rod 44 and which is slotted so that it can be clamped on the rod by drawing the two sides of the slot together. The rod has a pin 48 which keeps the clamp member 46 from sliding off the end thereof. A similarly slotted (or split-ring) clamp member 54 is disposed on the arm or rod 56, which is rotatably and slidably mounted within clamp member 54 and which has a pin 52 to prevent the member 54 from sliding off the end thereof.

Figure 4:
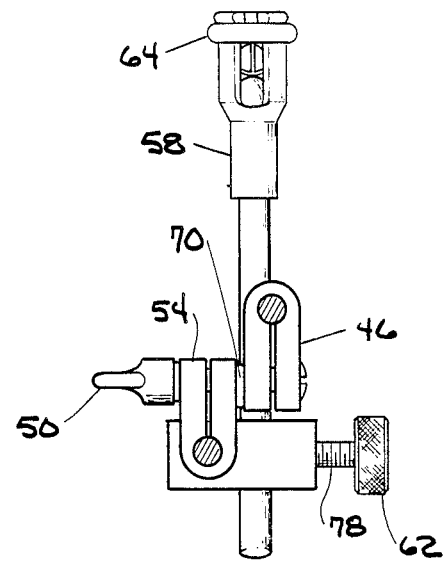
FIG. 4 is a sectional view taken on line 4—4 of FIG. 3.
Figure 3:
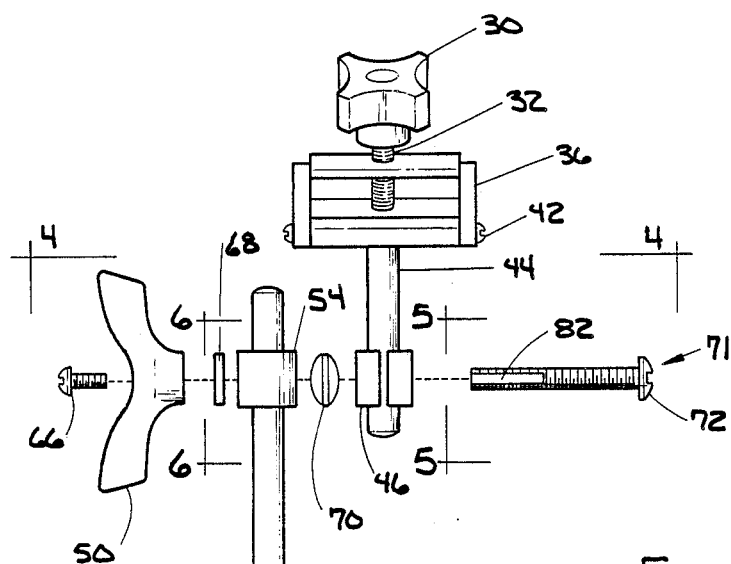
FIG. 3 is a detail view of FIG. 2, parts being exploded.
Figure 5:
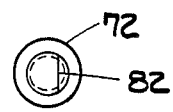
FIG. 5 is a detail view looking on line 5—5 of FIG. 3.
Figure 6:
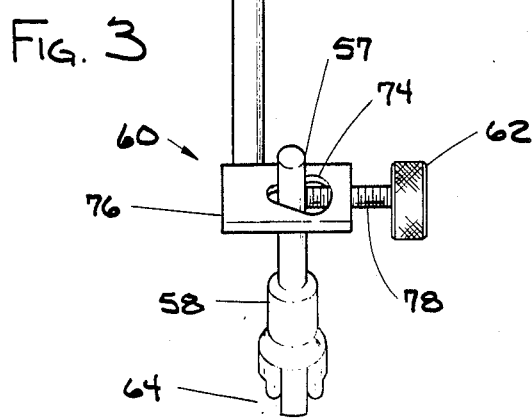
FIG. 6 is a detail view of 68 looking in the direction of line 6—6 of FIG. 3.

A single draw bolt 71 is passed through both slotted clamp members as best shown in FIGS. 3 and 4. Each side of each slotted clamp member has a half-bore of sufficient size to pass the bolt 71. If desired, however, the slot side adjacent the head 72 can be threaded so that the bolt 71 and that side act as a unitary mass. A wing nut 50 is provided to tighten up the bolt 71. A double convex washer 70 is placed between the two slotted clamp members 46 and 54. If desired, the opposed faces of the clamp members 46 and 54 can be countersunk so that only the center portion of the washer 70 shows, as in FIG. 4. A portion of the bolt 71 may be flattened as at 82, FIG. 5 and the washer 68 similarly configured at 80 so that its does not rotate on the bolt 71 when the wing nut 50 is tightened up. A screw bolt 66 can be threaded in a threaded bore interior of bolt 71 to keep the wing nut 50 from inadvertently coming off. Thus, when the wingnut is tightened up, the pivotal or rotative angle of the arms 44 and 56 about the axis of bolt 71 is fixed, the sides of the clamp members 46 and 54 are drawn together and fixed in whatever position they may have been placed in by their rotation and sliding on and about the rods 44 and 56, vice versa, and their rotation about the draw bolt 71.

On rod 56, preferably adjacent the end of rod 56, is located clamp 60 for clamping the cardio-valve holding member 68 by its attached arm 57, together constituting a cardio-valve holding means. The clamp 60 comprises a block 76 which, as shown, is rigidly affixed to the end of arm 56 but which, in other embodiments need not be rigidly mounted at or near the end thereof but may be slidably and/or rotatably mounted but securable in a rigid and/or fixed position on arm 56 as by a threaded screw or clamp means similar to elements 60 or one-half of the double clamp means previously described.

This block has a bore 74 therein which is preferably but not necessarily normal to the rod 56 so that, when the arm or rod 57 of the holding member 58 is clamped in the bore 74, it is rigidly secured and preferably essentially normal to the rod 56. The bore 74 has a larger end which tapers to a smaller end. A knob 62 turns a screw 78 which is threaded through the large end and which, when turned, forces the rod 57 into contact with the tapered sides of bore 74.

The cardio-valve holding member 58 is adapted releasably to receive a cardio-valve having a plastic-fabric ring 64 which is sutured into the heart to hold the replacement valve in place. At this point the rod 57 is released from the clamp 60 and the holder 58 removed from the replacement valve. If desired, the rod 57 can be connected to a pusher head 59 so that, when the head 58 is moved relative thereto, the replacement valve is in effect pushed out of the head 58 or, more precisely, the head 58 is pulled off of the replacement valve. If desired the head 58 and the rod 57 can be threaded (not shown) so that turning of the rod 57 relative to the head 58 will cause the pusher 59 to move relative to the head 58. It is thus in any event possible to remove the head 58 with a minimum of stress on the sutures.

Thus the invention makes it possible effectively to replace a damaged heart valve with a replacement valve by placing the replacement valve in a holding means, adjusting the holding means into a position where the replacement valve can be sutured into the heart, and clamping it rigidly in that position relative to the operating table, so that the suturing can then be effected without danger of inadvertent displacement of the replacement valve or of the sutures securing the same in place.

In conclusion, from the foregoing, it is apparent that the present invention provides a novel cardio-valve assist means suitable for use in cardio-valve replacement surgery, as well as a novel method of cardio-valve replacement surgery with employment of the said assist means, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:

1. A method for performing cardio-valve replacement surgery which comprises:
    affixing a replacement cardio-valve in a cardio-valve holding means;
    adjusting said cardio-valve holding means to a substantially fixed position where the replacement cardio-valve can be sutured into the heart;
    clamping said holding means to a support means in a position in proximity to an operating table; and clamping said holding means rigidly in said position relative to said operating table and;
    then suturing the replacement cardio-valve into the heart.

2. A method of claim 1 wherein said cardio-valve holding means is clamped in a clamp means comprising a bore having a larger end tapering to a smaller end and screw means threaded into movement toward said smaller end.

3. A method of claim 1 in which the adjusting and clamping steps are effected by a cardio-valve assist unit which comprises:
    first clamp means adapted to be clamped in a fixed position relative to an operating table;
    first arm means affixed to said first clamp means and rigidly projecting therefrom;
    second arm means;
    double-clamp means for connecting said second arm means to said first arm means;
    said double-clamp means comprising two parts mounted for rotation one relative to the other, one of which is adapted to receive said first arm means for slidable movement therein and the other of which is adapted to receive said second arm means for slidable movement therein and single clamping screw means adapted simultaneously to clamp said two parts on said arm means in any position to which they may have been adjusted and said two parts in fixed relation to each other; and third clamp means mounted in said second arm means for clamping a cardio-valve holding means to said second arm in rigid relation thereto;

whereby, when a cardio-valve holding means having a cardio-valve therein is clamped in said third clamp means, the cardio-valve can be placed in position for suturing into the heart and held firmly in that position until the suturing is complete.

4. A method of claim 3 wherein said arm means are also mounted for rotatable movement in said clamp means.

5. A method of claim 3 wherein said cardio-valve holding means is clamped in position substantially normal to said second arm.

* * * * *